United States Patent [19]

Dormandy, Jr.

[11] Patent Number: 5,779,672

[45] Date of Patent: Jul. 14, 1998

[54] DUAL VALVE DETACHABLE OCCLUSION BALLOON AND OVER-THE-WIRE DELIVERY APPARATUS AND METHOD FOR USE THEREWITH

[75] Inventor: Ray H. Dormandy, Jr., Pleasanton, Calif.

[73] Assignee: Interventional Therapeutics Corporation, Fremont, Calif.

[21] Appl. No.: 812,375

[22] Filed: Mar. 5, 1997

Related U.S. Application Data

[63] Continuation of Ser. No. 421,767, Apr. 14, 1995, abandoned.

[51] Int. Cl.[6] ............................................. A61M 29/00
[52] U.S. Cl. ........................................ 604/96; 606/195
[58] Field of Search .................................. 606/192, 194, 606/195; 604/96, 97, 99, 103, 247

[56] References Cited

U.S. PATENT DOCUMENTS

| | | | |
|---|---|---|---|
| 4,364,392 | 12/1982 | Strother et al. | 606/195 |
| 4,545,367 | 10/1985 | Tucci | 606/195 X |
| 4,819,637 | 4/1989 | Dormandy, Jr. et al. | 128/325 |
| 5,181,921 | 1/1993 | Makita et al. | 606/195 |
| 5,222,970 | 6/1993 | Reeves | 606/195 |
| 5,304,123 | 4/1994 | Atala et al. | 604/54 |

Primary Examiner—Corrine M. McDermott
Attorney, Agent, or Firm—Morrison & Foerster

[57] ABSTRACT

Dual valve detachable occlusion balloon for use in an artificial vessel embolization for using a delivery catheter adapted to receive a fluid for inflating the balloon. The delivery catheter has proximal and distal extremities and a flow lumen extending from the proximal extremity to the distal extremity and has a balloon inflation orifice in the distal extremity in communication with the flow lumen. The valve comprises a cylindrical body of an elastomeric material having first and second open ends and a bore extending between the first and second open ends. A first valve is mounted in the first end of the cylindrical body. A second valve is mounted in the second end of the cylindrical body. The first and second valves face in opposite directions in the bore. The first and second valves are in a normally sealed position to prevent the escape a fluid under pressure in the bore of the cylindrical body. The first and second valves are formed to permit movement to an open position to permit the delivery catheter to be inserted therethrough and form a substantially fluid-tight seal therewith with the balloon inflation orifice being disposed in the bore between the first and second valves so that fluid introduced into the bore through the delivery catheter to inflate the balloon cannot escape. The valves are formed to move to a closed sealing position upon removal of the delivery catheter from the balloon.

10 Claims, 1 Drawing Sheet

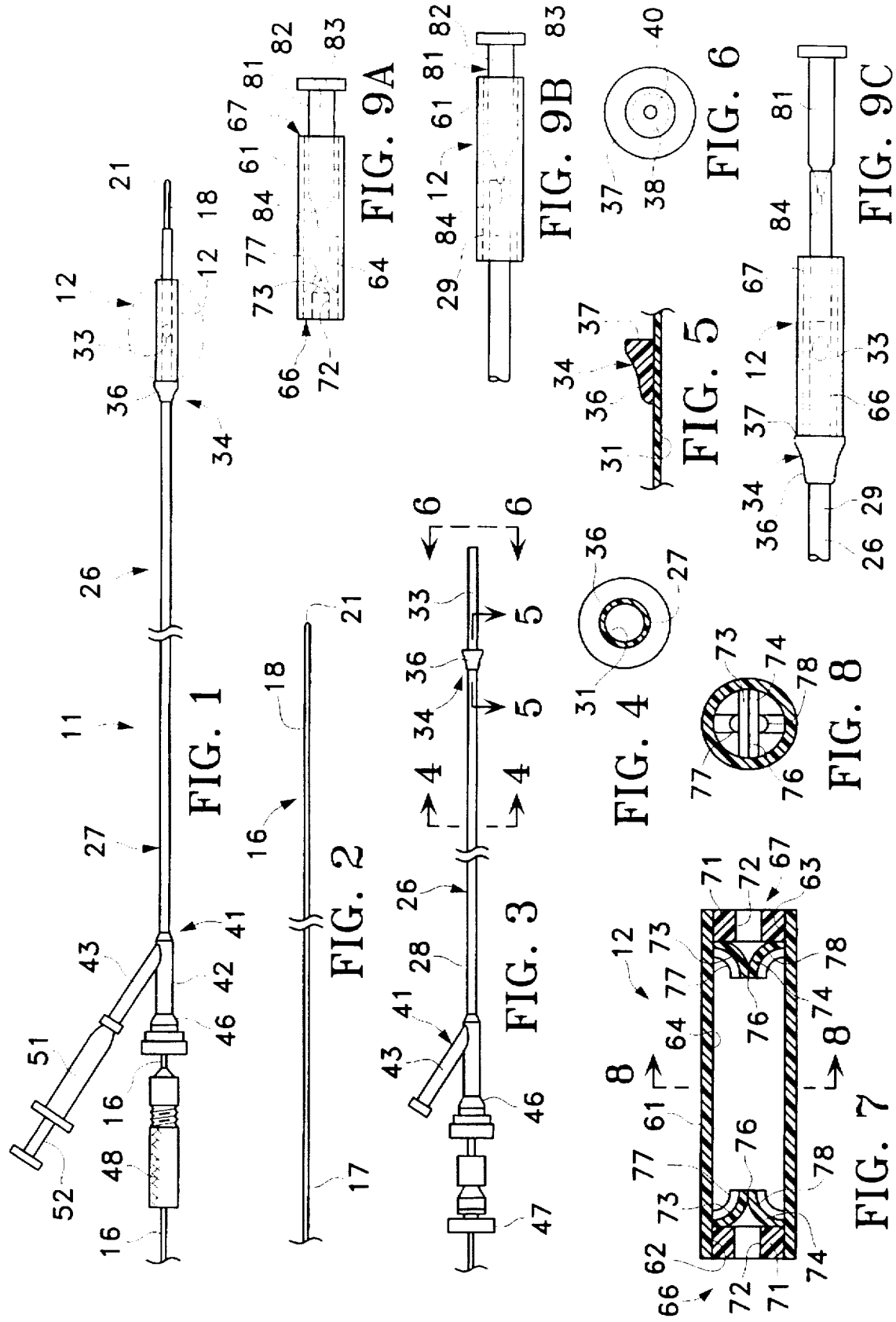

5,779,672

DUAL VALVE DETACHABLE OCCLUSION BALLOON AND OVER-THE-WIRE DELIVERY APPARATUS AND METHOD FOR USE THEREWITH

This application is a continuation of application Ser. No. 08/421,767, filed Apr. 14, 1995, now abandoned.

This invention relates to a dual valve detachable occlusion balloon and over-the-wire delivery apparatus and method for use therewith.

In U.S. Pat. No. 4,819,637, there is disclosed a detachable balloon and a balloon delivery catheter for delivering the detachable balloon. In the construction therein disclosed, the balloon shell covers the opening in the tip of the delivery catheter which makes it necessary in order to position the detachable balloon to advance the distal extremity of the delivery catheter carrying the detachable balloon into the desired location without being able to utilize a previously positioned guide wire to aid in positioning of the delivery catheter. This limits the capability of such a delivery catheter with the balloon mounted thereon to negotiate tight bends or to traverse a tortuous course in a blood vessel. There is therefore a need for a detachable occlusion balloon and a delivery catheter which can be utilized with a guide wire to provide an over-the-wire delivery apparatus and system for the detachable occlusion balloon.

In general, it is an object of the present invention to provide a dual valve detachable occlusion balloon for use in artificial embolization which can be utilized in an over-the-wire delivery apparatus and an over-the-wire delivery apparatus and method which utilizes such a dual valve detachable occlusion balloon.

Another object of the invention is to provide a dual valve detachable occlusion balloon which can be readily inflated.

Another object of the invention is to provide a dual valve detachable occlusion balloon which can be readily mounted upon the distal extremity of the balloon delivery catheter.

Another object of the invention is to provide a dual valve detachable occlusion balloon from which the balloon delivery catheter can be readily removed after the balloon has been inflated.

Another object of the invention is to provide an over-the-wire delivery apparatus which makes it possible to deliver more than one balloon and different sizes of balloons if desired.

Additional objects and features of the invention will appear from the following description which the preferred embodiments are set forth in detail in conjunction with the accompanying drawings.

FIG. 1 is a side-elevational view of an over-the-wire delivery apparatus and a dual valve detachable occlusion balloon mounted thereon incorporating the present invention.

FIG. 2 is a side-elevational view of the guide wire shown in FIG. 1.

FIG. 3 is a side-elevational view of the balloon delivery catheter shown in FIG. 1.

FIG. 4 is an enlarged cross-sectional view taken along the line 4—4 of FIG. 3.

FIG. 5 is a sectional view taken along the line 5—5 of FIG. 3.

FIG. 6 is an enlarged end view of the balloon delivery catheter shown in FIG. 3 looking along the line 6—6 of FIG. 3.

FIG. 7 is a greatly enlarged cross-sectional view of the dual valve detachable occlusion balloon shown in FIG. 1.

FIG. 8 is a cross-sectional view taken along the line 8—8 of FIG. 7.

FIGS. 9A, 9B, and 9C are illustrations showing the manner in which a mandrel is used for mounting the dual valve detachable occlusion balloon on the distal extremity of the balloon delivery catheter.

In general, the dual valve detachable occlusion balloon is for use in artificial vessel embolization in conjunction with a delivery catheter that is adapted to receive fluid for inflating the balloon. The delivery catheter has proximal and distal extremities and a flow lumen extending from the proximal extremity to the distal extremity and having a balloon inflation orifice in the distal extremity. The balloon is comprised of a cylindrical body of elastomeric material having first and second open ends and a bore extending between the first and second open ends. A first valve is mounted on the first end of the cylindrical body and faces inwardly into the bore and a second valve is mounted on the second end of the cylindrical body and faces inwardly into the bore in a direction opposite the first valve. The first and second valves are formed to permit movement to an open position and to permit the delivery catheter to be inserted therethrough and to form a fluid-tight seal with the balloon inflation orifice being disposed in the bore between the first and second valves so that fluid can be introduced into the bore through the delivery catheter to inflate the balloon. The valves are formed to move to a closed sealing position upon removal of the balloon delivery catheter from the balloon and are normally in a sealed position to prevent the escape of fluid under pressure in the bore of the cylindrical body.

More particularly as shown in FIGS. 1–8 of the drawings, the over-the-wire delivery apparatus 11 for the delivery of the dual valve detachable occlusion balloon 12 consists of a guide wire 16 which can have a suitable length ranging from 150–300 centimeters with the later dimension being desirable when an exchange procedure is utilized as hereinafter described. The guide wire 16 as shown in FIG. 2 is provided with proximal and distal extremities 17 and 18. The guide wire can be of a suitable diameter, as for example ranging from 0.008" to 0.060" and typically 0.0014". The guide wire 16 can be of a substantially conventional type with the exception that a sealing member 21 is mounted on the distal extremity which can be of any suitable configuration but as shown can be in the form of a ball or a sphere. The sealing member or ball 21 can be formed of a silicone adhesive and can be sized ranging from 0.010" to 0.080" depending upon the balloon delivery catheter being utilized. Because the ball is somewhat flexible, it is able to creep into the tip of the catheter to form a good seal with respect to the tip of the catheter 26.

The guide wire 16 is for use with a balloon delivery catheter 26. The balloon delivery catheter 26 consists of a flexible elongate tubular member 27 formed of a suitable medical grade plastic. The flexible elongate tubular member 27 can be of a suitable size, as for example ranging from 0.020" to 0.110" and can have a suitable length ranging from 20–160 centimeters. As shown, the flexible elongate tubular member 27 has proximal and distal extremities 28 and 29 and can be extruded to a centrally disposed lumen 31 extending from the proximal extremity 28 to the distal extremity 29. The lumen 31 is sized so that it is adapted to be passed over the proximal extremity 17 of the guide wire 16. Thus the lumen 31 can have a suitable size ranging from 0.010" to 0.065".

The flexible elongate tubular member 27 of the balloon delivery catheter 26 is provided with a balloon inflation orifice 33 in the distal extremity 29 in communication with the central lumen 31 and is positioned so that when the distal extremity of the flexible elongate member 27 is disposed within the balloon 12 as hereinafter described, fluid introduced into the lumen 31 and passing from the orifice 33 can be used for inflating the balloon 12. To aid in positioning of the distal extremity 29 of the flexible elongate tubular member 27 in the appropriate position so that the orifice 33 is properly disposed within the balloon 12, a shaped ring 34 is provided on the exterior surface of the flexible elongate tubular member 27 proximal of the orifice 33 to assist in positioning the proximal end of the balloon 12. It can be formed of a radiopaque material such as a metal-filled plastic. The shaped ring 34 is provided with a curved proximal annular surface 36 and a steep distal annular surface 37. The proximal surface 36 minimizes the possibility of interference during withdrawal of the catheter while the distal steep surface 37 forms a firm and positive contact with the proximal extremity of the balloon 12. The outer diameter of the shaped ring 34 is intended to be slightly larger than the diameter of the balloon 12 in the uninflated state. Thus when the shaped ring 34 is at the proximal extremity of the balloon 12, the orifice 33 is in the proper position for inflating the balloon 12.

The distal extremity 29 of the flexible elongate tubular member 27 is provided with an annular bead 38 (see FIG. 6) formed of a suitable material such as a silicone adhesive or polyethylene to form a valve seat for sealing valve member 21. The annular bead 38 defines a small opening 40 through which the guide wire 16 can passed.

A conventional Y-adapter 41 is mounted on the proximal extremity 28 of the balloon delivery catheter 26 and is provided with a central arm 42 and a side arm 43. A conventional Touhy Borst adapter 46 is mounted on the central arm 42 through which guide wire 16 can be extended. The adapter 46 is provided with a knob 47 which can be rotated to move a sealing ring (not shown) provided within the adapter between open and sealing positions with respect to the guide wire 16. A convention torquer 48 is removably mounted on the guide wire 16 proximal of the adapter 46 to aid in positioning the guide wire 16. A conventional syringe 51 is removably mounted on the side arm 43 and carries a fluid which can be used for inflating the balloon by operation of the plunger 52 of the syringe. The side arm 43 is provided with a flow passage (not shown) which is in communication with the central lumen 31 through which the guide wire 16 extends.

The dual valve detachable occlusion balloon 12 has many characteristics which are similar to the detachable balloon described in U.S. Pat. No. 4,819,637. The dual valve detachable occlusion balloon 12 consists of a cylindrical body 61 which can be formed of a soft distensible silicone elastomer material that provides enhanced elongation and expansion characteristics. It can have a wall thickness prior to expansion ranging from 0.003" to 0.012". The cylindrical body 61 can have a suitable length ranging from 0.100" to 0.600". Typically, the balloon 12 when inflated will have a wall thickness of 0.005" or less.

The cylindrical body 61 is provided with first and second open ends 62 and 63 with a cylindrical bore 64 extending therebetween. A first valve 66 is mounted on the first open end 62 and faces into the bore 64 in one direction and a second valve 67 is mounted in the second open end 63 of the cylindrical body 61 and faces into the bore 64 in an opposite direction.

The first and second valves 66 and 67 are of a type which form a fluid-tight seal so that a fluid under positive pressure within the cylindrical bore 64 cannot pass through the valves. The valves 66 and 67 are also formed so that they can permit a cylindrical element, as for example the flexible elongate tubular member 27 of the balloon delivery catheter 26 to pass therethrough and form a seal with respect thereto to prevent a fluid under pressure within the cylindrical bore 64 from exiting through the valves. The valves 66 and 67 are also formed so that they will return to a closed sealing position upon removal of the flexible elongate tubular member 27. By way of example, the valves 66 and 67 can be of a suitable type, as for example the self-sealing mitre or duck bill valves disclosed in U.S. Pat. No. 4,819,637. As described in said U.S. Pat. No. 4,819,637, the valves 66 and 67 can be formed of a cylindrical base 71 having a cylindrical passage 72 therein. The base 71 can be formed of a suitable material such as a silicone elastomer into which there has been incorporated a suitable radiopaque agent such as barium sulfate. A pair of leaflets or vanes 73 and 74 are bonded to the base 71 in a curvilinear manner as shown, for example a silicone adhesive. If desired, the leaflets can be color coded to identify the attachment force which is provided by the valve base 71. The leaflets or vanes 73 and 74 form a mitre seal 76 which extends diametrically of the base 71 and also of the cylindrical body 61. Reinforcing rods 77 are provided on the leaflets 73 and 74 to yieldably retain the leaflets 73 and 74 in a sealing position.

As can be seen from the drawings and in particular from FIG. 7, the first and second valves 66 and 67 face in opposite directions so that both of the seals 76 face inwardly into the bore 64 so that when a positive pressure is created within the bore 64, the positive pressure will urge the leaflets 73 and 74 into a tighter sealing engagement with each other.

In FIGS. 9A, 9B, and 9C there is shown an apparatus and method for loading the dual valve detachable occlusion balloon 12 onto the distal extremity 29 of the balloon delivery catheter 26. This is accomplished by the use of a mandrel 81. The mandrel 81 is generally cylindrical in shape and has a diameter ranging from 0.020" to 0.120" depending upon the size of the catheter. Typically the diameter of the mandrel should be slightly larger than the outside diameter of the catheter onto which the balloon is to be mounted. It also should have a length which is shorter than the balloon length. Assuming a balloon having a length of 0.280", the mandrel would have a length of approximately one-half that of the balloon or about 0.140". The mandrel can be of a suitable material such as stainless steel or Teflon. The mandrel is provided with a cylindrical body 82 which has a head 83 mounted on one end and which has the other end tapered to a conical-like point 84 in the form of a porpoise-like nose. The mandrel 81 has a diameter which is greater than the outside diameter of the catheter 26.

The stiff mandrel 81 is introduced through the second valve 67 of the balloon 12 as shown in FIG. 9A. The distal extremity 29 of the balloon delivery catheter 26 is then advanced through the first valve 66 of the balloon 12 until the conical point 84 of the mandrel 81 enters the lumen 31 of the balloon delivery catheter as shown in FIG. 9B. The tip 84 is held in engagement with the distal extremity of the catheter 26 and then while holding the catheter 26 in one hand, the balloon 12 is advanced proximally off of the mandrel 82 and further onto the distal extremity 29 of the catheter 26 as shown in FIG. 9C until the proximal extremity of the first valve 66 is in firm contact with the radially extending surface of the shaped ring 34 on the catheter 26. This ensures that the orifice 33 is properly located in the cylindrical bore 64 between the valves 66 and 67.

In order to facilitate placement of the balloon on the distal extremity 29 of the flexible elongate tubular member, a silicone lubricant can be provided in the first and second valves 66 and 67.

Operation and use of the over-the-wire delivery apparatus 11 with the dual valve detachable occlusion balloon 12 may briefly be described as follows. Let it be assumed that the apparatus 11 has been shipped to a hospital or physician with one or more balloons 12 of the same or of various sizes and with a mandrel 81. Typically, a balloon 12 will not be supplied on the distal extremity of the catheter 26 because the leaflets of the valves might take a permanent set which would inhibit them making a good seal. Thus when it is intended to do a procedure in which one or more balloons are to be utilized, one of the balloons 12 is selected and placed on the mandrel 81 as hereinbefore described and is then inserted over the distal extremity 29 of the balloon delivery catheter 26. Alternatively, the balloon 12 can first be placed over the distal extremity 29 of the balloon delivery catheter 26 and then the mandrel 81 inserted to aid in having the distal extremity 29 of the balloon delivery catheter traversing the second valve 67 of the balloon 12. The correct position for the balloon 12 on the distal extremity 29 can be ascertained by observing the radiopaque shaped ring 34 which is placed at an appropriate distance from the balloon inflation orifice 33. When positioned adjacent the shaped ring 34 as shown in FIG. 1, the balloon inflation orifice 33 is disposed between the first and second valves 66 and 67.

Let it be assumed that a procedure such as that described in U.S. Pat. No. 4,819,637 has been undertaken by introducing the guide wire 16 into a vessel, as for example the femoral artery and that a guiding catheter (not shown) and a introducer catheter (not shown) have been advanced into the desired location and that it is now appropriate to utilize the balloon delivery catheter 26 of the present invention hereinbefore described with a deflated detachable balloon 12 mounted thereon. Typically, the delivery catheter 26 can be flushed with a saline solution to ensure that all air is removed from the central lumen 31. With the guide wire 16 still in place with its distal extremity 18 being disposed in the location in which it is desired to position the occlusion balloon 12 the distal extremity 29 of the flexible elongate tubular member 27 of the balloon catheter 26 is threaded over the proximal extremity 17 of the guide wire 16 and advanced into and through the catheters already in place. As the balloon delivery catheter 26 is being advanced with the balloon 12 thereon, it is possible to introduce a contrast agent. This can be readily accomplished by introducing the contrast agent by the use of the syringe 51 through the central lumen 31 around the guide wire 16 so that it exits immediately distal of the balloon 12 to make it possible to visualize the vessel structure distal of the balloon 12 while the balloon is being advanced.

When the balloon 12 has been advanced to near the desired position for embolization, additional contrast agent can be introduced to obtain a very localized image of the location in which the balloon 12 is to be positioned. Assuming that the balloon 12 is now in the appropriate position, the guide wire 16 can be grasped by the other hand and pulled proximally to cause the silicone metal sealing ball 21 carried by the guide wire 16 to come into contact with the annular bead valve seat 38 carried by the distal extremity 29 of the flexible elongate member 27 to form a good seal therewith. Since the valve seat 38 is formed of a silicone adhesive or other relatively soft material, it will creep and form a good seal with respect to the ball 21.

The position of the balloon 12 can be relatively accurately ascertained by viewing the same under X-rays because of radiopaque markers (not shown) placed on the ends of the balloon 12 and on the balloon delivery catheter 26. Also to ascertain the location, the balloon 12 can be filled with a contrast agent through the syringe 51 to fill the space in the bore 64 to visualize a balloon without inflating the balloon. After the correct position has been ascertained, the contrast agent may be allowed to remain or can be withdrawn from the balloon and a suitable solidifying agent or material can be introduced into the balloon through the syringe 51 of the type described in U.S. Pat. No. 4,819,637.

As soon as the balloon has been inflated the desired amount, the balloon delivery catheter 26 can be withdrawn to permit the balloon to become detached therefrom. As soon as the flexible elongate tubular member 27 of the balloon delivery catheter 26 passes from the second valve 67 that second valve 67 will seal followed by sealing of the first valve 66 when the flexible elongate tubular member 27 is withdrawn therefrom. This withdrawal of the balloon delivery catheter 26 typically is accomplished by withdrawing the guide wire 16 at the same time. The balloon catheter 26 and the guide wire 16 can then be removed from the vessel in a conventional manner leaving the balloon 12 in place to form a permanent implant to occlude the vessel in which the balloon 12 has been implanted.

In connection with the present invention it should be appreciated that the dual valve detachable occlusion balloon rather than being filled with a solidifying agent can be filled and inflated with a contrast agent. This is desirable in many situations because the radiopaque contrast agent is biocompatible with the body of the patient in the event there is any leak or balloon rupture.

The use of a radiopaque contrast agent is also beneficial and it helps to identify the outer shape of the balloon after it has been inflated as well as the ends of the valves. This helps to check the effectiveness of the balloon 12 for a period of time by being able to assess its dimensions over time.

Since the balloon 12 is formed of an elastomeric material and has a very thin wall, it, when inflated, will be in close intimate contact with the vessel wall. The balloon, because of its thin wall is very tolerant of the vessel and helps to maintain the viability of the vessel over long periods of time thereby avoiding necrosis in the vessel wall which could permit hemorrhaging and/or movement of the balloon in the vessel.

It is apparent from the foregoing that there has been provided an over-the-wire delivery apparatus for a dual valve detachable occlusion balloon which makes it possible to deliver the occlusion balloon through vessels with sharp bends and vessels which are tortuous.

In accordance with the present invention it should be appreciated that if desired, it is possible to deliver more than one balloon with the over-the-wire delivery apparatus herein described merely by removing the balloon delivery catheter 26 and leaving the guide wire 16 in place and then inserting another balloon on the distal extremity 29 and advancing it to the desired location in the manner hereinbefore described. In order to permit balloon delivery catheters 26 to be interchanged or to place another balloon on a delivery catheter which has already delivered its balloon, a guide wire 16 can be used in conjunction with an exchange wire (not shown) of a type well-known to those skilled in the art to increase the effective length of the guide wire or alternatively the guide wire 16 can be of a greater length, as for example twice the length of a conventional guide wire to facilitate the delivery of more than one balloon or balloons of different sizes.

What is claimed is:

1. A dual valve detachable occlusion balloon for use in an artificial vessel embolization for use with a delivery catheter adapted to receive a fluid for inflating the balloon, the delivery catheter having proximal and distal extremities and a flow lumen extending from the proximal extremity to the distal extremity and having a balloon inflation orifice in the distal extremity in communication with the flow lumen, the balloon comprising a cylindrical body of an elastomeric material having first and second open ends and a bore extending between the first and second open ends, a first duck-bill valve mounted in the first open end of the cylindrical body, a second duck-bill valve mounted in the second open end of the cylindrical body, said first and second valves facing in opposite directions into the bore, said first and second duck-bill valves each comprising an elastomeric cylindrical base member having an axial bore extending therethrough, a pair of leaflets bonded to the cylindrical base in a curvilinear manner and forming a mitre seal extending diametrically of the cylindrical base, said first and second duck-bill valves being in a normally sealed position to prevent the escape of a fluid under pressure in the bore of the cylindrical body, said first and second duck-bill valves being formed to permit movement to positions to permit said delivery catheter to be inserted through said first and second duck-bill valves and form a substantially fluid-tight seal therewith and so that the balloon inflation orifice is disposed in the bore between the first and second duck-bill valves whereby fluid introduced into the bore through the delivery catheter to inflate the balloon cannot escape, said first and second duck-bill valves being formed to move to a closed sealing position upon removal of the delivery catheter from the balloon.

2. A balloon as in claim 1 wherein said leaflets of said valves are color coded to identify the attachment force provided, by the cylindrical base when a delivery catheter extends through the bore in the cylindrical base.

3. A balloon as in claim 2 wherein said elastomeric material is a silicone elastomer.

4. An over-the-wire delivery apparatus comprising:
   a.) a balloon delivery catheter comprising a flexible elongate tubular member having proximal and distal extremities and having a lumen extending therethrough from the proximal to the distal extremity and providing an opening at the distal extremity, the distal extremity being provided with a balloon inflation orifice spaced proximally of said opening and in communication with the lumen in the flexible elongate tubular member, circumferental sealing member carried by the distal extremity of the flexible elongate tubular member and disposed in said opening and forming a smaller opening,
   b.) a guide wire having a distal extremity, said guide wire extendible through said lumen and through said smaller opening and having a sealing member carried by the guide wire distal extremity adapted to engage the sealing member carried by the distal extremity of the flexible elongate member and
   c.) a balloon detachably mountable on the distal extremity of the flexible elongate tubular member thereby and overlying the balloon inflation orifice and having a sealing member for establishing sealing contact with the flexible elongate tubular member whereby when the sealing member of the guide wire is in engagement with the circumferential sealing member, the balloon can be inflated by introducing a fluid through said lumen and through the balloon inflation orifice.

5. Apparatus as in claim 4 wherein the balloon is further comprised of a cylindrical body of elastomeric material having first and second open ends and a bore extending between the first and second open ends and first and second valves mounted in the first and second ends respectively for forming said sealing means, said first and second valves facing in opposite directions so that fluid under pressure in the bore cannot escape from the bore through the first and second valves.

6. Apparatus as in claim 5 together with a mandrel having a cylindrical body and having proximal and distal extremities and having a porpoise-like tip on the distal extremity of the same, said tip being adapted to be inserted through one of the first and second valves in the balloon and to extend into the bore in the balloon to permit the balloon to be pushed off of the mandrel and slid onto the distal extremity of the flexible elongate tubular member.

7. A method for placing a dual valve occlusion balloon having first and second spaced-apart valves on the distal extremity of a balloon delivery catheter of the type having a distal extremity and having a lumen extending therethrough and having a balloon inflation orifice proximal of the distal extremity and in communication with the lumen by use of a mandrel having a cylindrical body with a distal extremity having a porpoise-like nose thereon comprising inserting the mandrel into the balloon by introducing the porpoise-like nose through the second valve, introducing the distal extremity of the balloon delivery catheter through the first valve, advancing the porpoise-like nose into the distal extremity of the balloon delivery catheter, advancing the balloon off of the mandrel and onto the distal extremity of the balloon delivery catheter so that the balloon inflation orifice is disposed within the balloon between the first and second valves.

8. A method for delivering an occlusion balloon to a site in a vessel to create an artificial embolization in the vessel comprising introducing a guide wire having a distal extremity so that the distal extremity of the guide wire is disposed in the vicinity of where a vessel embolization is to be undertaken, providing a balloon delivery catheter having a distal extremity with a lumen extending through the distal extremity and having a balloon inflation orifice proximal of the distal extremity in communication with the lumen, mounting a dual valve balloon onto the distal extremity of the balloon delivery catheter so that it is in registration with the balloon inflation orifice carried by the balloon delivery catheter, advancing the distal extremity of the balloon delivery catheter with the balloon thereon over the guide wire and to the region where the balloon is to be positioned, inflating the balloon, detaching the balloon from the distal extremity of the balloon delivery catheter and removing the delivery catheter and the guide wire from the vessel while leaving the balloon in place in the vessel.

9. A method as in claim 8 together with the step of introducing a radiopaque contrast fluid through the lumen in the delivery catheter distal of the balloon to visualize the region in the vessel in which the balloon is being advanced.

10. A method as in claim 9 together with the step of sealing off the lumen at the distal extremity of the balloon delivery catheter so that the radiopaque contrast fluid cannot escape from the distal extremity of the lumen and introducing additional radiopaque contrast fluid into the lumen and into the balloon to cause inflation of the balloon, visualizing the location and the conformation of the balloon by viewing the radiopaque contrast fluid while it is in the balloon, removing the delivery catheter from the balloon and removing the guide wire from the balloon and, thereafter removing the delivery catheter and the guide wire from the vessel.

* * * * *